United States Patent [19]

Batz et al.

[11] 4,184,848

[45] Jan. 22, 1980

[54] ELIMINATING TURBIDITY IN SERUM UNDERGOING PHOTOMETRIC ASSAY

[75] Inventors: Hans-Georg Batz; Brigitte Draeger, both of Tutzing; August W. Wahlefeld, Weilheim; Günter Weimann, Tutzing; Wolfgang Gruber, Tutzing-Unterzeismering, all of Fed. Rep. of Germany

[73] Assignee: Boehringer Mannheim GmbH, Mannheim-Waldhof, Fed. Rep. of Germany

[21] Appl. No.: 836,111

[22] Filed: Sep. 23, 1977

[30] Foreign Application Priority Data

Jun. 1, 1977 [DE] Fed. Rep. of Germany ....... 2724757

[51] Int. Cl.$^2$ .................... G01N 33/16; G01N 31/14
[52] U.S. Cl. .................... 23/230 B; 23/901; 23/925; 435/10; 252/408; G01N/21/22; 435/16
[58] Field of Search ............... 23/230 B; 195/103.5 R; 260/410.6; 252/408

[56] References Cited

U.S. PATENT DOCUMENTS

| | | | |
|---|---|---|---|
| 3,847,482 | 11/1974 | Sokol | 23/230 B |
| 3,853,465 | 12/1974 | Rush | 23/905 |
| 3,958,939 | 5/1976 | Jones | 23/230 B |
| 4,011,045 | 3/1977 | Bonderman | 195/103.5 R |

FOREIGN PATENT DOCUMENTS 2327894 8/1975 Fed. Rep. of Germany.

*Primary Examiner*—Sidney Marantz
*Attorney, Agent, or Firm*—Sprung, Felfe, Horn, Lynch & Kramer

[57] ABSTRACT

An agent for the elimination of turbidity in serum, especially in serum samples wherein photometric measurements are to be made, consisting essentially of one or more mono- or di-esters of polyethylene glycol and fatty acids of 9 to 14 carbon atoms with at most 8 ethylene oxide units per fatty acid moiety in the molecule, said esters having an HLB value of from 8 to 12.8.

9 Claims, 3 Drawing Figures

ELIMINATING TURBIDITY IN SERUM UNDERGOING PHOTOMETRIC ASSAY

The invention relates to an agent for the elimination of turbidity in serum, especially in serums in which photometric measurements are to be made. In further aspects, the invention relates to a process for the preparation of said agent, and to a method of using same.

Photometric clinical-chemical or other analytic tests are often difficult or impossible in very turbid solutions. Where very turbid solutions, especially turbid serums, are involved, other methods of measurement have hitherto been indicated.

German Patent Publication (Auslegeschrift) No. 23 27 894 discloses an agent for the clarification of turbid serums, which consists of polyethylene glycol laurates of 9 to 20 ethylene oxide units. These are substances which completely dissolve in water and have HLB (hydrophilic-lipophilic balance) values above 13.3. It has been found, however, that such an agent only slightly clarifies solutions which are made slightly turbid by serums. It does not permit a complete elimination of the turbidity.

The invention provides a turbidity-elimination which is capable of substantially eliminating turbidity, or at least one that will suffice for the performance of a photometric measurement. Particularly, the invention provides an agent which will permit clinical chemical tests to be performed on turbidity forming serums, even in continuously operating automatic test apparatus.

The invention is based on the surprising discovery that polyethylene glycol esters which do not dissolve clearly in water—i.e., which themselves produce turbidity—eliminate turbidity far more efficaciously than the known agents which form clear water solutions.

The agent for the elimination of turbidity interfering with photometric measurements in serums in accordance with the invention is thus characterized in consisting essentially of one or more mono- or di-esters of polyethylene glycol and fatty acids of 9 to 14 carbon atoms, having a maximum of 8 ethylene oxide units in the molecule, and, if desired, one or more solubility improvers. The ester or ester mixture has an HLB value of between 8 and 12.8.

Lauric acid is preferred in the framework of the invention as the acid component. However, good results are also obtained with pelargonic acid, capric acid, undecylic acid, tridecylic acid and myristic acid.

Particularly advantageous results are achieved if the content of esters of less than 5, and especially of 3 to 4, ethylene oxide units in the molecule amounts to from 10 to 40%, by weight, of the entire agent.

The ester component of the agent of the invention is not itself clearly soluble in the serum determination samples, and therefore leads to the occurrence of additional turbidity when it is added to a serum. But, depending on the composition of the serum, not only the turbidity caused by the addition of the agent of the invention but also the original turbidity disappear within a few minutes, and in many cases an entirely clear serum is obtained. In other cases, however, it is necessary additionally to use a solubility improver. Suitable solubility improvers are those substances which are capable of clearly dissolving the agent of the ivention without themselves interfering with the photometric measurement. Preferably, low alkanols, especially ethanol, of one to three carbon atoms, glycols of up to six carbon atoms, polyglycols of up to 8 ethylene oxide units, and/or tensides which by themselves are not capable of clarifying the turbidity in the serum, are used as solubility improvers. Among the tensides, it is again the polyethylene glycol esters that are preferred. Those polyethylene glycol ethers of alkanols having 8 to 16 carbon atoms in the molecule are preferred which contain 8 to 14 ethylene oxide units.

It is important to the agent of the invention that the impurities be kept to a minimum. Especially, the agent should be free of traces of aldehyde and acid. Commercial polyethylene glycol esters therefore are not suitable for the agents of the invention, as a rule, without further refinement. In this refinement, any polyglycols which they might contain must also be separated. This is possible, for example, by extracting the aqueous solutions with halogenated hydrocarbons, such as trichlorethylene, for example.

However, the esters of the agent of the invention are preferably prepared by a method which excludes undesirable impurities and yields the desired composition with regard to the frequency distribution of the ethylene oxide groups. In accordance with the invention, therefore, a method of preparing the aforesaid agent is characterized by reacting polyethylene glycols of 3 to 8 polyethylene oxide units in the molecule with boric acid in a molar ratio of 3:1, heating the product with fatty acid of 9 to 14 carbon atoms, then hydrolyzing by the addition of water, extracting with a polar, organic solvent that is not miscible with water, separating the organic phase, drying, treating with aluminum oxide, and finally removing aluminum oxide and solvent.

The esterification of polyethylene glycols with a fatty acid via the tris-ethylene glycol orthoboric acid ester is in itself disclosed in "Tenside," 12, 313 to 315 (1975). The known process, however, always results in a product containing undesirable impurities. By the procedure of the invention, however, a product of sufficient purity is obtained directly. The solvent extraction is performed preferably from a salt-saturated aqueous solution. Suitable extractants are especially halogenated solvents such as chloroform.

The reaction with boric acid is performed preferably at a temperature between 80° and 100° C. over a period of at least 7 hours in a water-jet vacuum.

Fatty acid polyethylene glycol esters prepared by the above-described method via the boric acid esters are especially suitable for the agent of the invention not only due to their superior purity, but also on account of their molecular weight distribution. That is to say, the components of low molecular weight of up to 5 ethylene oxide units in the molecule react preferentially, so that the optimum is shifted towards the products of lower degree of condensation.

It is also possible, however, to use refined commercial esters of the above-named kind for the preparation of the agent. In the latter case, esters of low molecular weight, that is, those of 3 and 4 ethylene oxide units in the molecule, are added preferentially. Suitable amounts are between about 5 and about 20% by weight.

In addition to the above-named essential components, the agent of the invention can also contain buffer solution and other additives which are inert with respect to serum components and commonly used in analysis systems, provided that tests are made to assure that they do not impair the action of the agent.

The agent of the invention is added in such amounts as to achieve the desired clarifying action. In general these amounts are between 0.1 and 5%, depending on the composition of the serum to be clarified, and the other reagents that are added to the serum. However, even smaller amounts may suffice, or larger amounts may be necessary, especially in the case of very lipemic serums.

If larger amounts are needed, it is often desirable to add a low alkanol (1 to 3 carbon atoms) or a glycol of up to 7 carbon atoms, or a polyglycol of up to 8 ethylene oxide units in the molecule, as a solubility improver. In this case the sensitivity of the components contained in the solution to alcohol must be taken into consideration. Especially when alcohol-sensitive enzymes are present, it is often better to add, instead, a tenside as solubilizer.

If, for example, glucose is to be determined by the glucose oxidase method, experience has shown that it will suffice to add an amount corresponding to 0.4% of the ester and 0.1 to 0.4% of the solubilizer, even if the optical determination is to be performed in the non-deproteinized serum. If, on the other hand, uric acid is to be determined in a turbid serum specimen by means of catalase and aldehyde dehydrogenase, it is necessary to add an amount of the agent corresponding to 3 weight-percent of ester.

If a tenside is used as a solubility improver, the amount to be added is to be kept as low as possible, because, although such an additive increases the solubility of the agent of the invention, it simultaneously impairs its turbidity-clarifying activity.

As already mentioned, the agent of the invention makes possible the elimination of turbidity in serum, this being accomplished even when the turbidity is very severe. In many cases only the addition of the agent of the invention can make it possible to perform optical determinations in serum specimens which have not been deproteinized. The agent is at the same time suitable for both substrate and enzyme determinations.

Furthermore, the agent of the invention is valuable also in the case of determinations in which, on account of the small amount of serum added, no great difficulty is involved, even though the serum is extremely turbid. When the agent of the invention is added, the parallel performance of a calibration series can often be dispensed with and the measurement can be made merely against the blank value of the reagents.

BRIEF DESCRIPTION OF THE DRAWINGS

Certain embodiments of the invention are illustrated in the drawings herein in which.

The following examples will further illustrate the invention:

EXAMPLE 1

Preparation of the Agent

Two moles of a polyethylene glycol of 3 to 8 ethylene oxide units are heated with 0.66 mole of boric acid in a water-jet vacuum for two hours at temperatures increasing to 90° C. The mixture is then held for another six hours at this temperature. After cooling, 0.2 mole of lauric acid and 2 grams of p-toluenesulfonic acid are added. Then, over a period of 2 hours the mixture is heated up to 100° C. and held at this temperature for another two hours. Then an equal volume of water is added and the mixture is stirred for one hour for hydrolysis. Then the solution is saturated with sodium chloride and extracted thrice by shaking with acetic ester. The combined ester phases are dried over sodium sulfate and then concentrated to about 100 ml. Then the solution is extracted by shaking with 50 g of basic aluminum oxide. A thin layer chromatogram is made to test for freedom from fatty acid. If traces of fatty acid are still present, the aluminum oxide treatment is repeated. Then the aluminum oxide is filtered out and the solvent is withdrawn, using an oil pump vacuum at the end.

The yield is from 60 to 90%, depending on the chain length of the polyethylene glycol.

By mixing 15 weight-parts of the lauric acid esters of polyethylene glycols of 3, 4 and 5 ethylene oxide units obtained as described above, with 20 weight-parts of the esters of 6 and 7 ethylene oxide units and about 5% of esters of eight ethylene oxide units, an agent is prepared in accordance with the invention.

EXAMPLE 2

A commercially obtainable mixture of polyethylene oxide and lauric acid ester containing about 4% of triethylene glycol esters, about 10% of tetraethylene glycol esters, about 15% of pentaethylene glycol esters and about 60% of hexa-, hepta- and octaethyleneglycol esters is extracted from the aqueous solution with trichlorethylene and then dried. To the product thus obtained, 8% of a triethylene glycol ester obtained in accordance with Example 1 is added.

EXAMPLE 3

Determination of Uric Acid 0.1 ml of a very turbid serum sample is mixed with one milliliter of a reagent solution of the following composition:

45 mM $K_4P_2O_7$, pH 8.5; $NAD_+$; catalase; aldehyde dehydrogenase; 5 vol.-% ethanol; 3 vol.-% of the agent of Example 2.

After standing for five minutes at room temperature the serum has clarified.

After the addition of the serum the extinction without the addition of the agent of the invention was $\Delta E_{334\ nm} = 2.239$. With the addition of the agent it was $\Delta E_{334\ nm} = 0.777$. The blank value of the reagents was: $\Delta E = 0.570$.

The determination of the uric acid in the clarified specimen is performed by adding uricase and measuring the change in the extinction ($\Delta E$) at 334 nm.

Figure 1:
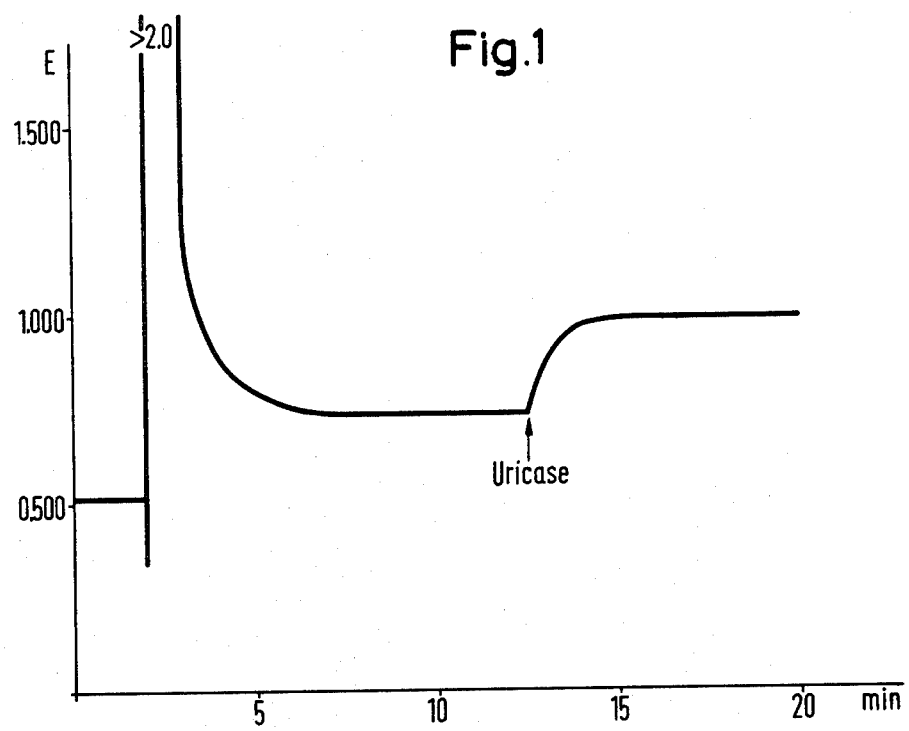
FIG. 1 is a plot of extinction values against time in a uricase determination.
Figure 2:
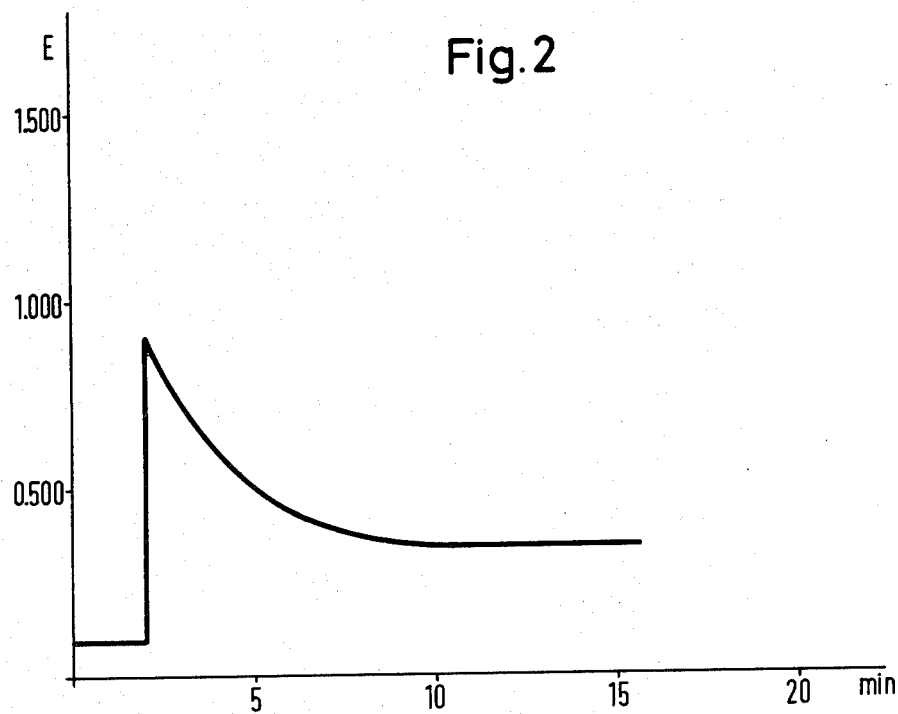
FIG. 2 is a plot of extinction values against time in a blood sugar determination.

FIG. 1 of the appended drawing shows the results of the measurement.

EXAMPLE 4

Blood Sugar Determination Without Deproteinization 0.02 ml of a very turbid serum sample are mixed with two milliliters of a reagent solution of the following composition:

0.2 M of tris-phosphate buffer, pH 8.0; phenol; p-aminoantipyrin, peroxidase (POD), glucose oxidase (GOD), 0.4 vol.-% polyhydroxyethylene dodecyl ether of about 8 ethylene oxide units, and 0.4 vol-% of the agent of Example 2.

The clarification of the sample and the development of the color are performed simultaneously; the change in the extinction is represented in FIG. 2 of the appended drawing.

EXAMPLE 5

Determination of Glutamate Oxalacetate Trans aminase (GOT)

0.5 ml of a turbid serum specimen is mixed with 3.1 ml of a reagent solution of the following composition: Phosphate buffer, pH 7.4; aspartate, NADH, lactate dehydrogenase (LDH), malate dehydrogenase (MDH), 2.85 vol.-% of the agent of Example 2.

Figure 3:
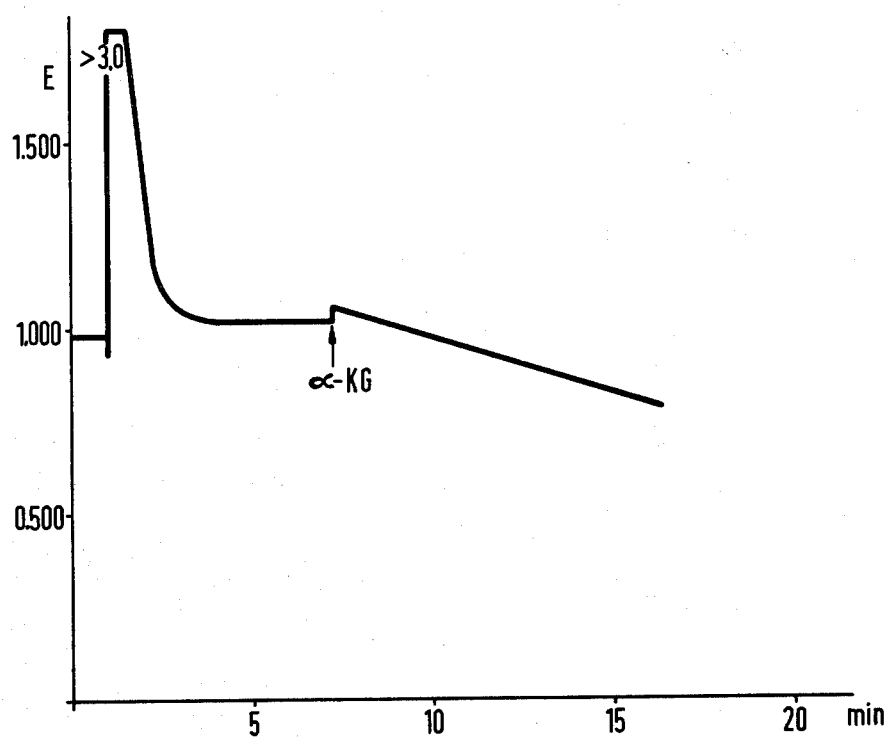
FIG. 3 is a plot of extinction values against time in a GOT determination.

The starting extinction of the serum was 1.870. After standing for 30 minutes, the specimen had cleared up, and the extinction was 0.820. The start was made by the addition of α-ketoglutarate and the change in the extinction at 366 nm was measured. FIG. 3 of the appended drawing shows the results of the measurement.

Particularly good results are obtained by proceeding as described in Examples 3 to 5, but using, instead of the agent of Example 2, an agent consisting of 60% of polyethylene glycol 300 laurate and 40% of polyethylene glycol 200 laurate, prepared in accordance with Example 1 from commercial polyethylene glycol 300 and 200, respectively. This agent has the following composition according to gas chromatographic analysis:

Monoglycol-L: 1.2%
Diglycol-L: 3.1%
Triglycol-L: 13.1%
Tetraglycol-L: 17.9%
Pentaglycol-L: 16.2%
Hexaglycol-L 15.1%
Heptaglycol-L: 12.4%
Octoglycol-L: 8.6%
Nonaglycol-L: 4.9%
Decaglycol-L: 2.6%
Undecaglycol-L: 1.1%
Dodecaglycol-L: 0.4%
Free polyglycol impurities less than 2%.

It will be understood that the specification and examples are illustrative but not limitative of the present invention and that other embodiments within the spirit and scope of the invention will suggest themselves to those skilled in the art.

What is claimed is:

1. Method for eliminating turbidity which interferes with photometric measurements in serum, which method comprises adding to the serum sample an agent comprising essentially an ester component consisting of at least one mono- or di-ester of polyethylene glycol and fatty acids of 9 to 14 carbon atoms with at most 8 ethylene oxide units per fatty acid moiety in the molecule, said ester component having an HLB value between 8 and 12.8, which agent is added to the serum sample in an amount of from 0.5 to 5 weight percent based on said serum sample.

2. Method as claimed in claim 1 wherein said serum sample contains turbidity interfering with performing photometric measurements thereon.

3. Method as claimed in claim 1 wherein said agent comprises an ester component consisting of lauric acid esters.

4. Method as claimed in claim 1 wherein said mono- or di-ester contains 10 to 40 weight percent of polyethylene glycol esters of 3 to 4 ethylene oxide units per fatty acid moiety in the molecule.

5. Method as claimed in claim 1 wherein said agent is free of acid and aldehyde traces.

6. Method as claimed in claim 1 wherein said agent also contains a solubility improver.

7. Method as claimed in claim 6 containing, as the solubility improver, a low alkanol of 1 to 3 carbon atoms, or a glycol of up to 7 carbon atoms or polyglycol of up to 8 ethylene oxide units.

8. Method as claimed in claim 6 wherein said solubility improver is one or more tensides which alone are not capable of eliminating or substantially clarifying turbidity.

9. Method as claimed in claim 8 wherein the tenside contains a polyethylene oxide ether of an alkanol of 8 to 16 carbon atoms in the molecule, which contains 8 to 14 polyethylene oxide units.

* * * * *